US011529300B2

(12) United States Patent
Kelly et al.

(10) Patent No.: US 11,529,300 B2
(45) Date of Patent: Dec. 20, 2022

(54) FORMULATIONS FOR ENHANCING SKIN FIRMNESS, DENSITY AND THICKNESS

(71) Applicant: JAMRM, LLC, Dallas, TX (US)

(72) Inventors: Tatiana Kelly, Westlake, TX (US); Alisar Salah Zahr, Dallas, TX (US); John Koch, Ft. Worth, TX (US); Nirmal Shah, Arlington, TX (US); Thu Quynh Nguyen, North Richland Hills, TX (US)

(73) Assignee: JAMRM, LLC, Dallas, TX (US)

( * ) Notice: Subject to any disclaimer, the term of this patent is extended or adjusted under 35 U.S.C. 154(b) by 0 days.

(21) Appl. No.: 16/502,789

(22) Filed: Jul. 3, 2019

(65) Prior Publication Data
US 2021/0000728 A1    Jan. 7, 2021

(51) Int. Cl.
| | |
|---|---|
| *A61K 8/64* | (2006.01) |
| *A61K 8/9794* | (2017.01) |
| *A61Q 19/08* | (2006.01) |
| *A61K 8/04* | (2006.01) |
| *A61K 8/9789* | (2017.01) |

(52) U.S. Cl.
CPC ............ *A61K 8/64* (2013.01); *A61K 8/04* (2013.01); *A61K 8/9789* (2017.08); *A61K 8/9794* (2017.08); *A61Q 19/08* (2013.01)

(58) Field of Classification Search
None
See application file for complete search history.

(56) References Cited

U.S. PATENT DOCUMENTS

| | | | | |
|---|---|---|---|---|
| 2007/0110731 | A1* | 5/2007 | Riley | A61K 36/8962 424/93.7 |
| 2010/0080764 | A1* | 4/2010 | Fox | A61K 8/68 424/60 |
| 2012/0058140 | A1* | 3/2012 | Ceccoli | A61K 8/9771 424/195.15 |
| 2015/0104485 | A1* | 4/2015 | Garcia Anton | A61K 9/06 424/401 |
| 2020/0046625 | A1* | 2/2020 | Van Den Nest | A61K 38/06 |

FOREIGN PATENT DOCUMENTS

CA        3045668      * 9/2019

OTHER PUBLICATIONS

Bradley, E. et al. Components of an OTC Antiaging Cosmetic Product Result in Partial Repair of Photoaged Skin . . . J of the American Academy of Dermatology 70(5, Suppl 1) AB15, May 2014. (Year: 2014).*
Grice et al., "The skin microbiome" Nat Rev Microbiol. Apr. 2011; 9(4): 244-253 (22 pages).
Wikipedia "Skin Flora" retrieved from https://en.wikipedia.org/w/index.php?title=skin_flora&oldid+903973783 (11 pages).
Wikipedia "Microbiota" retrieved from https://en.wikipedia.org/w/index.php?title=Microbiota&oldid=903119975 (10 pages).

* cited by examiner

*Primary Examiner* — Ralph J Gitomer
(74) *Attorney, Agent, or Firm* — Stephen Y. Liu; Carstens, Allen & Gourley, LLP

(57) ABSTRACT

Provided are formulations that interact with the skin microbiome of a human patient such that when applied topically in therapeutically effective amounts at prescribed intervals, the formulations cause an increase in skin firmness, density, smoothness, elasticity and thickness resulting in a skin appearance that reflects overall skin health. In exemplary embodiments formulations include, without limitation, the following active components acting in concert with each other: a prebiotic component, a peptide component, a matrix metalloproteinases (MMPs) inhibitor component; and an antioxidant component; all present in a carrier base. The exemplary embodiments may be in the form of a cream, a lotion, a serum, or a hydrogel that facilitates delivery of these active components into the skin.

24 Claims, 6 Drawing Sheets
(5 of 6 Drawing Sheet(s) Filed in Color)

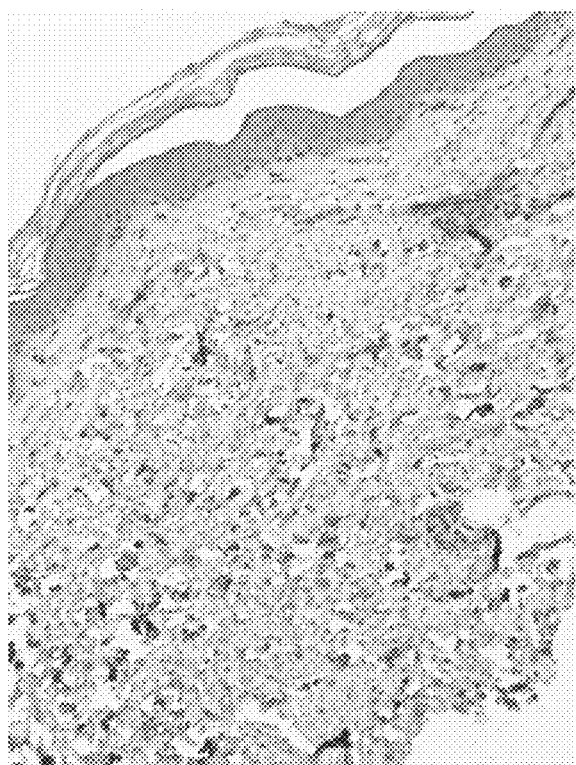 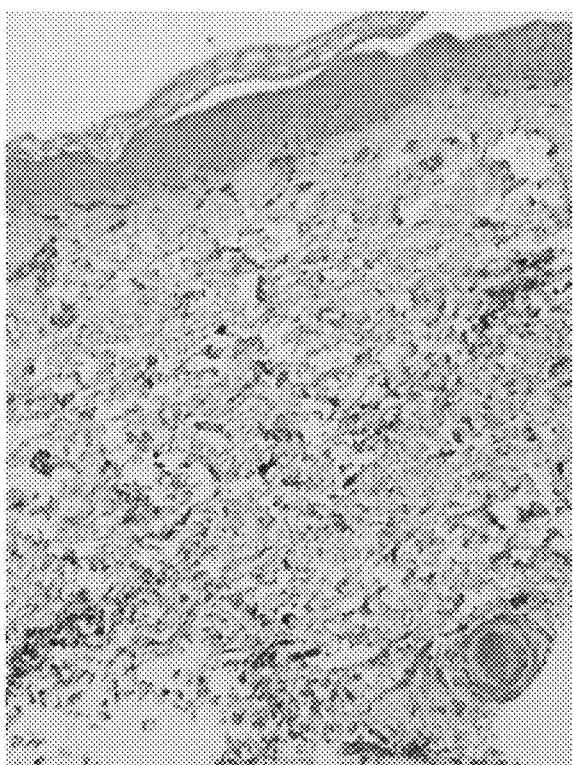
FIG. 4A                    FIG. 4B

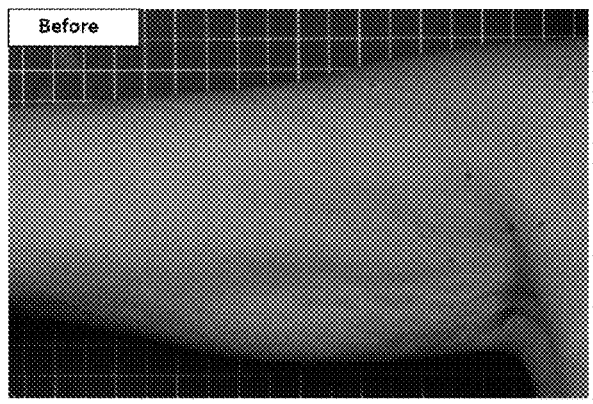 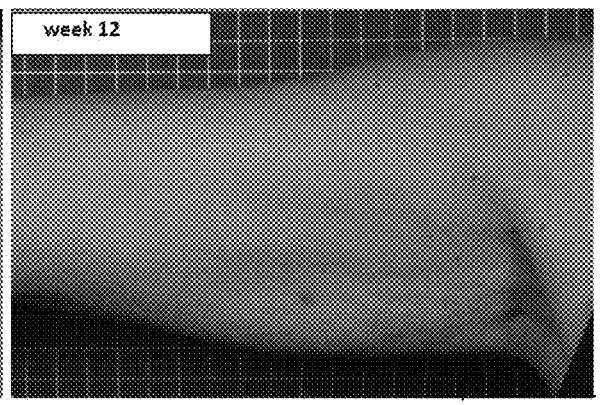
FIG 5A                                  FIG. 5B

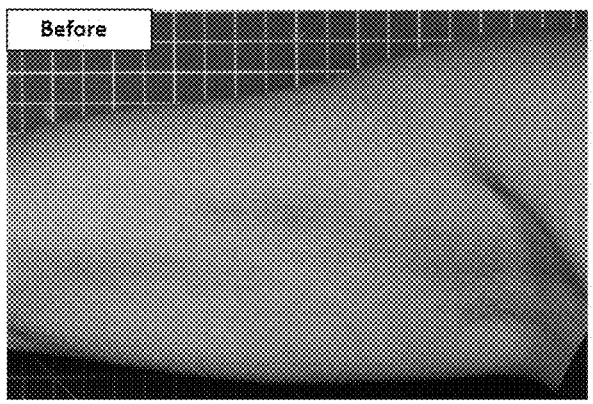
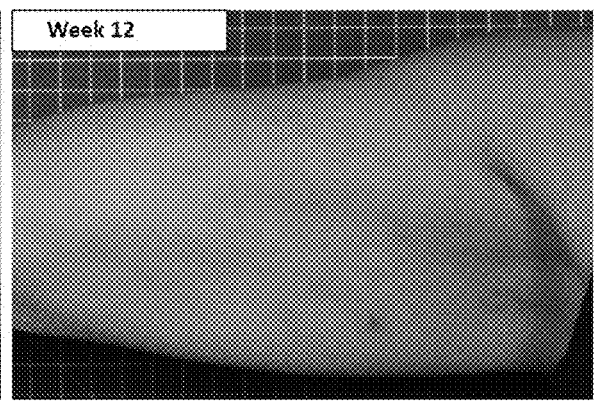
FIG. 6A                    FIG. 6B

FORMULATIONS FOR ENHANCING SKIN FIRMNESS, DENSITY AND THICKNESS

BACKGROUND

1. Field of the Invention

The inventions relate to formulations that are topically applied to human skin, both facial as well as body skin, that protect the skin from stressors and that improve a range of skin properties including skin density, skin thickness, and elasticity, while reducing skin crepiness and sagging, when applied in a therapeutic amount at prescribed intervals.

2. Description of the Related Art

Human skin is a multi-layered tissue, often referred to as the "largest organ in the body." It is complex, both in terms of structure, being multi-layered of varying porosity, and supplied with innumerable capillaries and blood vessels. Further complications are caused by factors in the surrounding environment that adversely affects the skin.

People have been aware of changes in the visible appearance and texture of human skin that take place over the years. And, for generations people have attempted to use cosmetic, topically-applied compositions to minimize these changes in appearance and texture or to reverse these changes.

More recently, there is an interest in the human microbiome, for reasons of health. According to Wikipedia.org (Biome), a microbiome is a mix of organisms that coexist in a defined space on a much smaller scale. For example, the human microbiome is the collection of bacteria, viruses, and other microorganisms that are present on or in a human body.

According to Wikipedia.org (Human Microbiota), the human microbiota is the aggregate of microorganisms that resides on or within any of a number of human tissues and biofluids, including the skin, mammary glands, placenta, seminal fluid, uterus, ovarian follicles, lung, saliva, oral mucosa, conjunctiva, biliary and gastrointestinal tracts. They include bacteria, archaea, fungi, protists and viruses. The human microbiome refers specifically to the collective genomes of resident microorganisms.

Humans are colonized by many microorganisms. Some microorganisms that colonize humans are commensal, meaning they co-exist without harming humans; others have a mutualistic relationship with their human hosts. Conversely, some non-pathogenic microorganisms can harm human hosts via the metabolites they produce. Certain microorganisms perform tasks that are known to be useful to the human host but the role of most of them is not well understood. Those that are expected to be present, and that under normal circumstances do not cause disease, are sometimes deemed normal flora or normal microbiota.

The Human Microbiome Project (HMP) was a National Institutes of Health (NIH) research initiative to improve understanding of the microbial flora involved in human health and disease. Launched in 2007, the first phase (HMP1) focused on identifying and characterizing human microbial flora. The second phase, known as the Integrative Human Microbiome Project (iHMP) was launched in 2014 with the aim of generating resources to characterize the microbiome and elucidating the roles of microbes in health and disease states.

Further, according to Wikipedia.org (Skin Flora), The term skin flora (also commonly referred to as skin microbiota) refers to the microorganisms which reside on the skin, typically human skin. Many of them are bacteria of which there are around 1000 species upon human skin from nineteen phyla. Most are found in the superficial layers of the epidermis and the upper parts of hair follicles. Skin flora are usually (but not always) non-pathogenic, and either commensal (are not harmful to their host) or mutualistic (offer a benefit). The benefits bacteria can offer include preventing transient pathogenic organisms from colonizing the skin surface, either by competing for nutrients, secreting chemicals against them, or stimulating the skin's immune system. However, resident microbes can cause skin diseases such as eczema, psoriasis, atopic dermatitis, and acne. For example, the article, "The Skin Microbiome," by Grice and Sigre, Nat. Rev. Microbiol. (Jan. 3, 2011) deals with several skin aliments that the authors postulate may be related to the skin microbiome. Grice & Sigre also state that the skin is colonized by a diverse milieu of microorganisms, most of which are harmless or even beneficial to their host. Colonization, according to the authors, is driven by the ecology of the skin surface, which is highly variable depending on topographical location, endogenous host factors and exogenous environmental factors. They then postulate that an enhanced understanding of the skin microbiome might be necessary to gain insight into microbial involvement in human skin disorders and to enable novel promicrobial and antimicrobial therapeutic approaches for their treatment.

The Grice & Sigre article asserts that disruptions in the balance between the host and the microorganism could result in skin disorders or infections. The authors argue that dysregulation of the skin immune response may manifest in several skin disorders for example, psoriasis, atopic dermatitis (AD), eczema and contact dermatitis. They do concede that how dysregulation affects and/or results from changes in the microbiota remains unclear.

According to the authors, the skin bacterium *P. acnes* is associated with the very common teenage malady acne, an inflammatory disorder of the pilosebaceous unit. The onset of puberty increases the preponderance of lipophilic microorganisms, especially *P. acnes*, which secretes lipases, proteases and hyaluronidases that injure the tissue lining of the pilosebaceous unit. However, the authors state that use of molecular methods to examine the bacterial component of acne has been limited, and a small sequencing study did not identify any novel acne-associated bacteria.

The authors further assert that atopic dermatitis (AD) is a chronic relapsing disorder that affects ~15% of US children and ~2% of adults and is also associated with microbial colonization and infection. The prevalence of AD has doubled or tripled in industrialized countries over the past three decades with no clear cause. The most common treatments for AD include topical or systemic antibiotics, and steroids. Dilute bleach baths to lower the bacterial load are effective in reducing clinical severity. No specific link has been identified between virulence factors expressed by *S. aureus* and flare-ups in patients with AD.

The authors note that *S. epidermidis* is a very common skin commensal, but it is also the most frequent cause of hospital-acquired infection on in-dwelling medical devices such as catheters or heart valves. After they gain entry, virulent strains of these organisms can form biofilms on catheters or other devices, which protects them from the host immune system and antibiotics. Increasing levels antibiotic resistance, particularly to oxacillin or methicillin, complicates treatment of *S. epidermidis* infections.

There is at this stage ongoing interest and research in the skin microbiome area in relation to the possibility that it might provide insights that would enable better, or at least alternative, strategies for the treatment of skin ailments that are challenging to treat or cure.

SUMMARY

The technology herein provides formulations that interact with the skin microbiome of a human patient such that when applied topically in therapeutically effective amounts at prescribed intervals, the formulations cause an increase in skin density as well as thickness resulting in a more firm and more smooth skin appearance that reflects good skin health. The formulations are effective on human facial skin as well as skin on other parts of the body that might need treatment, including but not limited to arms, legs, hands, neck, torso and back.

In exemplary embodiments, there are provided formulations that include, without limitation, the following components: a prebiotic component, a bioavailable peptide component, a matrix metalloproteinases (MMPs) inhibitor component, and an antioxidant component; all present in a carrier base. The exemplary embodiments may be in the form of an emulsion such as a cream, a lotion, a serum or a gel that is suitable to deliver these active components into the skin at the region where the active components are needed to carry out their treatment functions.

The formulations in accordance with the present technology include components that reduce skin stressors through scavenging or quenching of free radicals and inhibition of MMPs. Further, it includes prebiotics to restore and maintain the skin microbiome and support the biodiversity of the skin microbiome. This results in limiting harmful MMPs such as collagenase and elastase production, which left unchecked causes breakdown of peptide bonds in proteins found in the extracellular matrix, such as collagen and elastin. In addition, the formulations include bioavailable peptides which can enhance the production of extracellular matrix proteins. And, the formulations include antioxidants that scavenges or quenches free radicals such as the superoxide anion, the hydroxyl radical, and peroxide radicals. Accordingly, the components of the formulations operate in concert at the epidermal and dermal layer level to provide several functions including protecting against the effects of skin stressors, restoring stressed skin tissue and improving both skin density as well as skin thickness.

In an exemplary embodiment, the formulation includes from about 0.001 to about 30 wt. % of the prebiotic component; from about 0.00002 to about 2.0 wt. % of the bioavailable peptide component; from about 0.001 to about 10 wt. % of the antioxidant component; and from about 0.001 to about 10 wt. % of the matrix metalloproteinases inhibitor component.

In another exemplary embodiment, the formulation includes from about 0.01 to about 25 wt. % of the prebiotic component; from about 0.002 to about 0.75 wt. % of the bioavailable peptide; from about 0.01 to about 5 wt. % of the matrix metalloproteinases inhibitor component; and from about 0.01 to about 5 wt. % of an antioxidant component.

In an exemplary embodiment, the prebiotic component includes, but is not limited to any one or more of: inulin, *Laminaria Digitata* Extract, *Chlorella* Vulgans Extracts, Saccharide Isomerate, and Manihut *Esculenta*.

In an exemplary embodiment, the bioavailable peptide component of the formulation includes but is not limited to any one or more of: Palmitoyl Tetrapeptide-7, Palmitoyl Tripeptide-5, Palmitoyl Hexapeptide-19, Trifluoroacetyl Tripeptide-2, N-Prolyl Palmitoyl Tripeptide-56 Acetate and Dipeptide Diaminobutyroyl Benzylamide Diacetate.

In an exemplary embodiment, the matrix metalloproteinases inhibitor component includes but is not limited to any one or more of: *Bambusa Vulgaris* leaf extract, *Bambusa Vulgaris* stem extract, *Pisum Sativum* extract, and *Apium Graveolens* Callus extract.

In an exemplary embodiment, the carrier base is an emulsion of oil-in-water or silicone-in-water, an emulsion of water-in-oil, or a hydrogel or a tinted emulsion. Further, the carrier base may comprise from about 40 to about 95 wt. % of the formulation.

In an exemplary embodiment, the formulation the prebiotic component is selected to support optimal biodiversity of the skin microbiome.

In an exemplary embodiment, the matrix metalloproteinases inhibitor component is selected to function in coordination with the prebiotic component. In addition, the matrix metalloproteinases inhibitor component (which may include a plurality of matrix metalloproteinases inhibitors) may be selected to inhibit a plurality of matrix metalloproteinases.

In an exemplary embodiment, the matrix metalloproteinases inhibitor component inhibits MMP-1, MMP-3, MMP-9 and MMP-12.

In an exemplary embodiment, the antioxidant component is selected to function in coordination with the prebiotic component. In addition, the antioxidant may be selected to inhibit a plurality of matrix metalloproteinases.

In an exemplary embodiment, the antioxidant scavenges or quenches free radicals such as the superoxide anion, the hydroxyl radical, and peroxide radicals.

The formulations, which provide a significant improvement in several measurable skin parameters in as soon as 4 weeks, may also include retinoids, proteins, vitamins, and ceramides.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages, of the present technology will become more readily appreciated by reference to the following Detailed Description, when taken in conjunction with the accompanying Figures that include illustrative graphs and color photos. The Figures, briefly described here below, are not to scale, are presented for ease of explanation and do not limit the scope of the inventions recited in the accompanying patent claims.

The patent or application file contains at least one drawing executed in color. Copies of this patent or patent application publication with color drawing(s) will be provided by the Office upon request and payment of the necessary fee.

Figure 1:
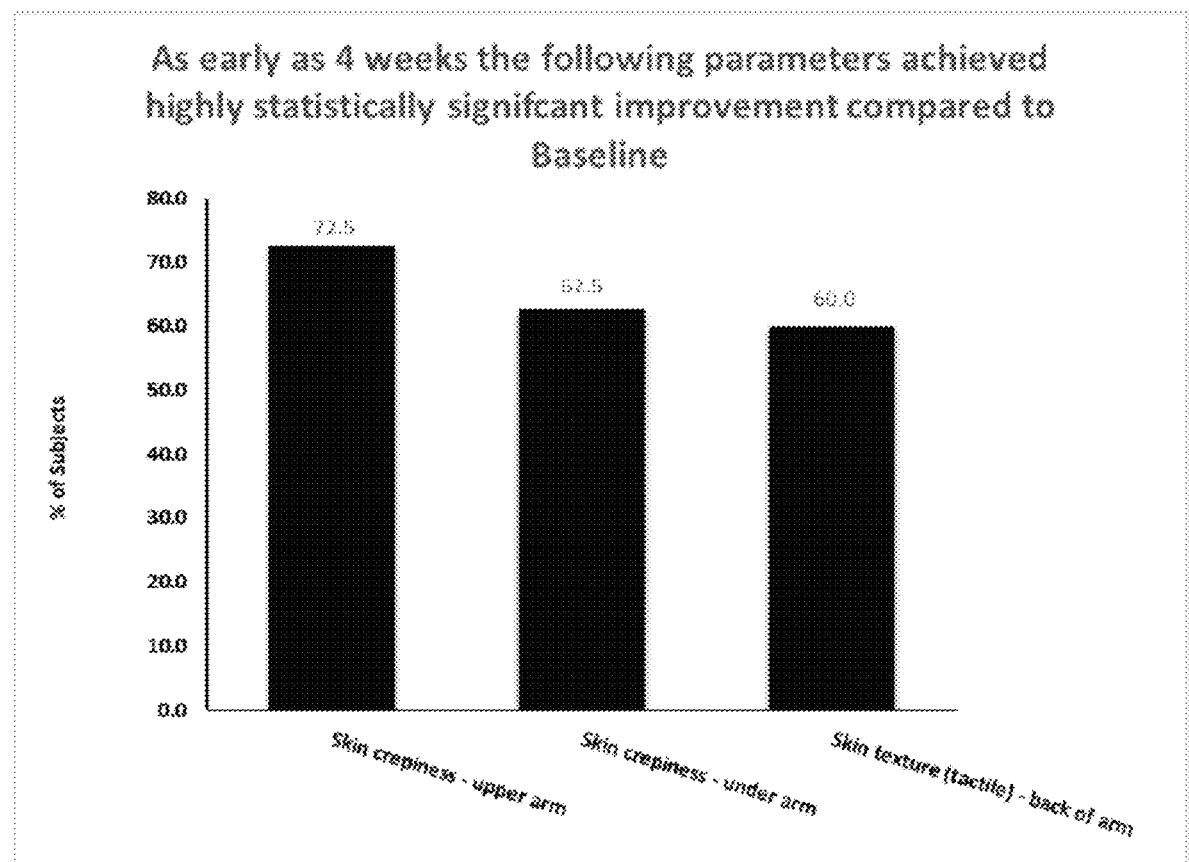

FIG. 1 is an illustrative depiction of a bar graph showing the improvement in skin crepiness, and skin texture in as early as 4 weeks of treatment with an exemplary embodiment of the formulation according to the invention.

Figure 2A:
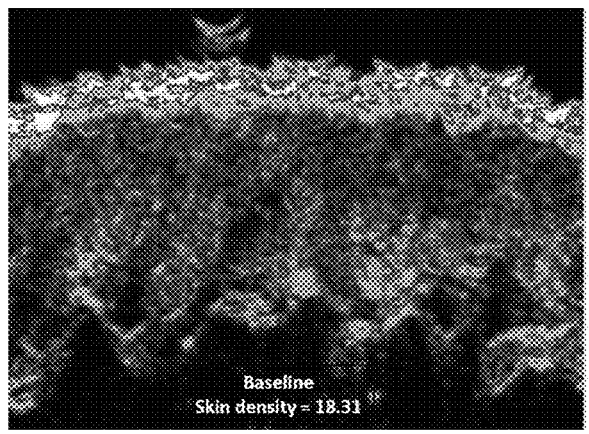

FIG. 2A is an ultrasound photomicrograph depicting in cross section baseline skin density (and thickness) of a person.

Figure 2B:
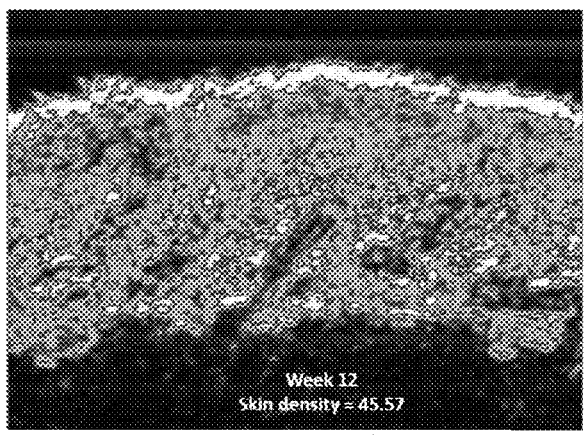

FIG. 2B is an ultrasound photomicrograph depicting in cross section skin density (and thickness) of the person of FIG. 2A after 12 weeks of treatment with an exemplary embodiment of the formulation according to the invention.

Figure 3A:
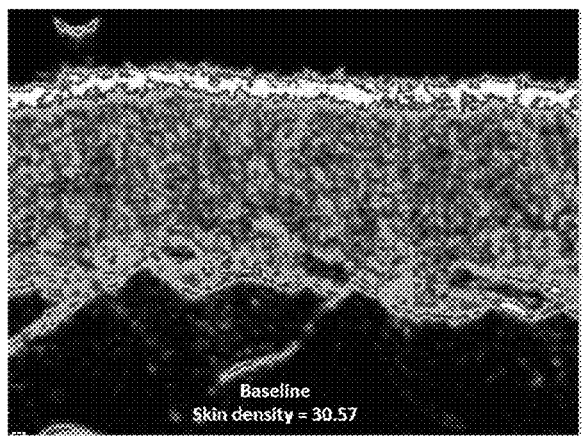

FIG. 3A is an ultrasound photomicrograph depicting in cross section baseline skin thickness of a person.

Figure 3B:
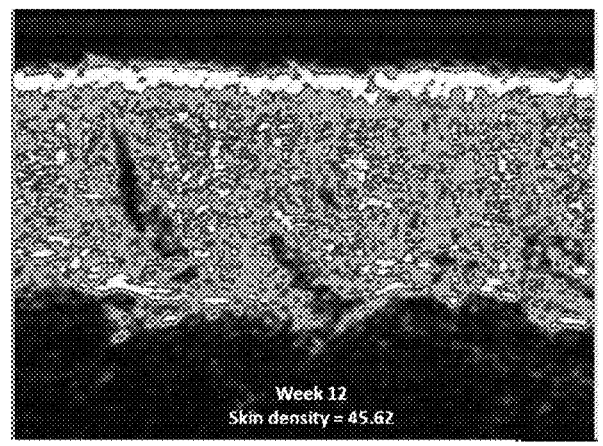

FIG. 3B is an ultrasound photomicrograph depicting in cross section the skin density of the person of FIG. 3A after 12 weeks of treatment with an exemplary embodiment of the formulation according to the invention.

FIG. 4A is a photomicrograph of a 3 mm punch biopsy skin sample of an upper arm underside of a person.

FIG. 4B is a photomicrograph of a 3 mm punch biopsy skin sample of an upper arm underside of the person of FIG. 4A taken after 12 weeks of treatment with an exemplary embodiment of the formulation, showing a darker and denser dermis from increased collagen production.

FIG. 5A is a photograph depicting an upper arm of a subject with sagging skin before treatment.

FIG. 5B is a photograph of an upper arm of the subject of FIG. 5A showing a reduction in sagging and crepiness of the skin after 12 weeks of treatment with an exemplary embodiment of the formulation.

FIG. 6A is a photograph of an upper arm of a subject having rough textured skin before treatment.

FIG. 6B is a photograph of the upper arm of the subject of FIG. 7A after 12 weeks of treatment with an exemplary embodiment of the formulation, showing improved skin smoothness.

DETAILED DESCRIPTION OF THE PREFERRED EMBODIMENTS

The patent or application file contains at least one drawing executed in color. Copies of this patent or patent application publication with color drawing(s) will be provided by the Office upon request and payment of the necessary fee.

The following non-limiting detailed descriptions of examples of embodiments of the invention may refer to appended Figure drawings and are not limited to the drawings, which are merely presented for enhancing explanations of features of the technology. In addition, the detailed descriptions may use particular terms of art, some of which are defined herein, as appropriate and as necessary for clarity.

There are presented topical formulations for human skin, including facial skin and body skin, and methods of applying these formulations in therapeutically effective amounts directly to areas of the human skin to both prevent as well as remediate damage caused by skin-stressors, by enlisting the human skin microbiome. The formulations are gently massaged into the skin, once or twice daily, as at intervals as prescribed for a particular patient or condition.

Human skin is exposed to several stressors in the normal course of modern day living. The stressors include, but are not limited to, for example, exposure to Ultra Violet (UV) light, Visible light, which is commonly known as blue light that is emitted in the solar spectrum as well as electronic monitors, allergens (contact), urban dust, and workplace and home stress that manifest in skin conditions. These stressors induce a reaction in the skin that increases the level of matrix metalloproteinases (MMPs). And the MMPs in turn disrupt peptide bonds in skin collagen and elastin.

According to the present technology, there is provided a formulation of a combination of prebiotics, bioavailable peptides, antioxidants, and selected plant-based extracts (matrix metalloproteinases inhibitors) that is delivered in therapeutically effective dose to the surface of the skin in a suitable carrier base. The formulation both restores and maintains the skin by utilizing properties of the microbiome of the skin. The prebiotic component of the formulation supports optimal biodiversity and the balance of microorganisms including bacteria in the skin microbiome. This limits the extent of harmful matrix metalloproteinases production when the person is subject to stressors, for example, it limits the production of collagenase (MMP-1). Collagenase causes undesirable breakdown of peptide bonds within collagen of the skin. Further, the MMP inhibitor component in the formulation, often derived from selected plant extracts, reduces multiple MMPs (e.g. MMP-1, MMP-3, MMP-9, MMP-12, etc.). The bioavailable peptide component of the formulation interrupts intercellular signaling and triggers the release of reactive chemicals to reconnect MMP-disrupted bonds in collagen.

Extrinsic stressors, as mentioned above, create free radicals or reactive oxygen species within the extracellular matrix and within cellular structures. These free radicals lead to upregulation of inflammatory events which directly or indirectly result in a stimulation of matrix metalloproteinases within the dermal structure. Antioxidants act to neutralize these free radicals and reactive oxygen species.

In the specification and claims, the use of the term "component" in the singular referring to a component of the formulation is intended to convey that the component may include a plurality of species. Thus, for example, the term "peptide component," inherently encompasses one peptide, and also encompasses a plurality of peptides that together make up the peptide component.

In the specification and claims, with reference to extracts described herein, the wt. % of a particular ingredient of the formulation refers to the weight of the named component in the extract, not the weight of the extract. Thus, for example a formulation having 1 wt. % of extract of *Pisum Sativum*, where the extract has a 5 wt. % concentration of *Pisum Sativum*, means 1×0.05=0.05 wt. % *Pisum Sativum* in the formulation. Thus, this would be described herein as 0.05 wt. % *Pisum Sativum* in the formulation.

The technology herein provides formulations that interact with and utilize properties of the skin microbiome of a human patient such that when applied topically in therapeutically effective dosage rates at prescribed intervals, the formulations cause an increase in skin density as well as thickness resulting in a more sculpted and smooth skin appearance. The formulations are effective on human facial skin as well as skin on other parts of the body that might need treatment, including but not limited to arms, legs, hands, neck, torso and back. The formulations provide a measurable improvement in skin properties in as early as 4 weeks of treatment. The formulations preferably have a pH in the range from about 4.0 to about 6.0.

The formulations according to the present technology, when applied in therapeutically effective dose at prescribed intervals, usually twice per day, provide several benefits. These include but are not limited to a reduction in skin crepiness, an improvement (increase) in skin elasticity, a reduction in the sagginess of skin, a reduction in skin photodamage, an improvement in skin smoothness (texture), increase in skin firmness, increase in skin density, an increase in epidermal thickness, and an improvement in overall skin appearance.

Treatments with the formulations of the present technology result in an increase of from about 20% to about 40% in collagen. An increase is manifested in several extracellular matrix protein, including Collagen IV. Treatments also show an improvement (increase in skin density from about 15 to about 30%. Treatments with the formulation show an improvement in skin moisturization of from 35% to about 45%. Treatments with the formulation show an increase in epidermal skin thickness of about 10 to about 30%.

The attached FIGURES illustrate the improvements achieved through treatment with exemplary embodiments of the formulations, and these results are discussed here below.

In an exemplary embodiment, the formulation includes from about 0.001 to about 30 wt. % of the prebiotic component; from about 0.00002 to about 2.0 wt. % of the bioavailable peptide component; from about 0.001 to about 10 wt. % of the antioxidant component; and from about 0.001 to about 10 wt. % of the matrix metalloproteinases inhibitor component.

In another exemplary embodiment, the formulation includes from about 0.01 to about 25 wt. % of the prebiotic component; from about 0.002 to about 0.75 wt. % of the bioavailable peptide; from about 0.01 to about 5 wt. % of the matrix metalloproteinases inhibitor component; and from about 0.01 to about 5 wt. % of an antioxidant component.

In an exemplary embodiment, the prebiotic component comprises at least one of inulin, *Laminaria Digitata* Extract, *Chlorella* Vulgans Extract and Manihut *Esculenta*. In an exemplary embodiment, the bioavailable peptide component of the formulation includes but is not limited to the following bioavailable peptides: Palmitoyl Tetrapeptide-7, Palmitoyl Tripeptide-5, Palmitoyl Hexapeptide-19, Trifluoroacetyl Tripeptide-2, N-Prolyl Palmitoyl Tripeptide-56 Acetate and Dipeptide Diaminobutyroyl Benzylamide Diacetate.

In an exemplary embodiment, the matrix metalloproteinases inhibitor component comprises at least one of *Bambusa Vulgaris* leaf extract, *Bambusa Vulgaris* stem extract, *Pisum Sativum* extract, and *Apium Graveolens* Callus extract.

In an exemplary embodiment, the carrier base is an emulsion of oil-in-water or an emulsion of water-in-oil, or a gel. Further, the carrier base may comprise from about 40 to about 95 wt. % of the formulation.

In an exemplary embodiment, the formulation the prebiotic component is selected to control for a desirable biodiversity of the skin microbiome.

In an exemplary embodiment, the matrix metalloproteinases inhibitor component is selected to function in coordination with the prebiotic component. In addition, the matrix metalloproteinases inhibitor component (which may include a plurality of matrix metalloproteinases inhibitors) may be selected to inhibit a plurality of matrix metalloproteinases.

In an exemplary embodiment, the matrix metalloproteinases inhibitor component inhibits MMPs that include but are not limited to any one or more of MMP-1, MMP-9, MMP-3, and MMP-12.

Exemplary embodiments of the formulations may also include one or more of pentylene glycol, dimethyl sulfone, urea, tetrahydropiperine, and lipophilic molecules including cholesterol or isopropyl myristate to facilitate delivery of active components of the formulation into the skin.

Antioxidants include but are not limited to any one of: *Vaccinium Vitis* Idea Fruit Extract, *Camellia* Sinesis Green Tea Leaf Extract, *Arnica, Astragalus Membranaceus*, Rutin, Hesperidin, and Naringin. Antioxidants also include polyphenols, bioflavonoids, tannins, and terpenoids. Some chemical molecules have multiple functions, and so an antioxidant can in some instances be the same as an MMP inhibitor. Thus, there can in some instances be overlap between the components.

In general it is preferred, but not essential, that the formulation be free of alpha hydroxy acid and ascorbic acid.

The formulation may also include skin growth factors, proteins, vitamins, and ceramides. The skin growth factors may include, but are not limited to: KGF (Keratinocyte growth factor: Palifermin CAS #162394-19-6); TGFβ (Transforming Growth Factor beta CAS #122304-04-5); VEGF (Vascular Endothelial Growth Factor Receptor-3 CAS #144638-77-7) and PDGF (Platelet Derived Growth Factor Platelet-activating factor [1-Hexadecyl-2-acetyl-glycero-3-phosphocholine CAS #74389-68-7] Platelet activating factor phosphatidate CAS #65154-06-5 [1-0-Alkyl-2-acetyl-sn-glyceryl-3-phosphorylcholine] Platelet Factor 1 CAS #62031-46-3, Platelet Factor 3 CAS #37270-93-2, or Platelet Factor 4 CAS #37270-94-3).

EXAMPLES

The following non-limiting examples illustrate at least some of the benefits of the formulations that include in combination at least: prebiotics, bioavailable peptides, antioxidants, and selected plant-based extracts (matrix metalloproteinases inhibitors) that is delivered in therapeutically effective dose to the surface of the skin in a suitable carrier base.

In FIG. 1 it is shown that in as early as 4 weeks of treatment, 72.5% ($p<0.001$) of subjects had a statistically significant decrease in upper arm skin crepiness; 62.5% ($p<0.001$) of subjects had a statistically significant decrease in under arm crepiness, and 60% ($p<0.001$) showed a statistically significant improvement in skin texture (smoothness) on the back of the arm. These measurements were made by a clinical grader using the modified Griffiths 10-point scale, where 0=none and 9=severe. The results found in FIG. 1 were measured against baseline value with a total of 40 subjects.

Test results also indicate that 90% of subjects (out of 40 subjects) using exemplary embodiments of the formulations had an about 42% improvement in in skin moisturization, after 12 weeks of twice daily use.

Test results also indicate that 83% of subjects (out of 40 subjects) using exemplary embodiments of the formulations had an average of an about 10% reduction in skin photodamage, after 12 weeks of twice daily use.

Test results indicate that 77% of persons (out of 40 subjects) showed a skin density increase of about 17% after 12 weeks of treatment with exemplary embodiments of the present formulations, based on results as evaluated by a clinical grader on 40 women, ages 40-60, after 12 weeks of twice daily use of on the arm. A single measurement was taken on each subject's upper arms using a 50 MHz ultrasonic transducer interfaced to a DUB 6100 OEM System (Taberna Pro Medicum, Luneburg, Germany). This exemplified in FIGS. 2A and 2B, where FIG. 2A is a ultrasound photomicrograph depicting, in cross section, baseline skin density (18.31) and thickness of a person. FIG. 2B is an ultrasound photomicrograph depicting in cross section skin density (45.57) and thickness of the person of FIG. 2A after 12 weeks of treatment with an embodiment of the formulation.

Even persons having a higher skin density baseline benefited from treatment as illustrated, for example, in FIGS. 3A and 3B. FIG. 3A is an ultrasound photomicrograph depicting in cross section baseline skin density of 30.57 of a subject; and FIG. 3B is an ultrasound photomicrograph depicting an improvement in skin density to 45.62 after 12 weeks of treatment with an exemplary embodiment of the formulation.

Clinical results also indicate an increase in several extracellular matrix protein including Collagen IV with an increase of about 29% in Collagen IV, which is an important protein in the Dermal-Epidermal Junction. Increase in collagen is in FIGS. 4A and B which are photomicrographs of biopsy skin samples. A 3-mm punch biopsy sample was taken from each upper arm (on the underside) at baseline and week 12. Biopsy samples were transferred into 10% formalin solution and embedded into paraffin. Immunohistochemistry was performed on paraffin embedded samples with human antibodies for Collagen IV, Collagen I, and elastin with a total of 10 subjects. FIG. 4A is at baseline, and FIG. 4B is of a biopsy taken after 12 weeks of treatment with an exemplary embodiment of the formulation. FIG. 4B shows a darker and denser dermis from increased collagen production.

Treatment of sagging skin with the formulations of the present technology also provided significant improvement in as early as 4 weeks of treatment that continued to 12 weeks when the test stopped. For example, FIG. 5A is a photograph depicting an upper arm of a subject with sagging skin before treatment. And, for comparison, FIG. 5B is a photograph of the upper arm of the subject of FIG. 5A showing a reduction in sagging of the skin after 12 weeks of treatment with an exemplary embodiment of the formulation. In the test, 83% of the subjects showed an average improvement of about 9% in reduction in sagging of the skin.

Clinical tests on 40 subjects that have non-smooth textured skin showed significant improvement in as early as 4 weeks of treatment with an exemplary embodiment of the present formulation, and continuing to 12 weeks of treatment, when the test stopped. For example, FIG. 6A is a photograph of an upper arm of a subject having rough textured skin before treatment. And, FIG. 6B is a photograph of the upper arm of the subject of FIG. 6A after 12 weeks of treatment with an exemplary embodiment of the formulation, showing improved skin smoothness. During the test, 97% of subjects showed an average improvement of about 21% in skin smoothness.

Test data from a clinical grader connects skin resiliency and elasticity, and shows that 77% of participants (40) showed an improvement in tactile skin elasticity of the underarm at week 12 with an improvement of 10% $p<0.001$. And, 90% of participants of showed an improvement in tactile skin elasticity of the upper arm at week 12 with an improvement of 15% $p<0.001$ The tests described above herein, each carried out over a 12-week period unless otherwise indicated, and exemplified by photographs in some instances, establish the efficacy of the unique complex formulations of combinations of peptides, prebiotics, antioxidants and matrix metalloproteinases inhibitors in treating for a variety of skin conditions by a novel approach of harnessing and improving the skin microbiome.

While examples of embodiments of the formulation have been presented and described in text, and some examples also by way of illustration, it will be appreciated that various changes and modifications may be made in the described technology without departing from the scope of the inventions, which are set forth in and only limited by the scope of the appended patent claims, as properly interpreted and construed.

The invention claimed is:

1. A formulation for topical application to human skin, the formulation comprising:
 a carrier base which is an emulsion of oil-in-water, or water-in-oil, or silicone-in-water, or a tinted emulsion, having dispersed therein components comprising:
 a prebiotic component;
 a bioavailable peptide component;
 an antioxidant component; and
 a matrix metalloproteinases inhibitor component.

2. The formulation of claim 1, wherein the prebiotic component comprises at least one of inulin, *Laminaria Digitata* Extract, *Chlorella* Vulgans Extracts, Saccharide Isomerate and Manihut *Esculenta*.

3. The formulation of claim 1, wherein the bioavailable peptide component comprises at least one of the following bioavailable peptides:
 Palmitoyl Tetrapeptide-7, Palmitoyl Tripeptide-5, Palmitoyl Hexapeptide-19, Trifluoroacetyl Tripeptide-2, N-Prolyl Palmitoyl Tripeptide-56 Acetate and Dipeptide Diaminobutyroyl Benzylamide Diacetate.

4. The formulation of claim 1, wherein the matrix metalloproteinases inhibitor component is selected from a genus comprising at least one of *Pisum, Babusa* and *Apium*.

5. The formulation of claim 1, wherein the matrix metalloproteinases inhibitor comprises at least one of *Bambusa Vulgaris* leaf extract, *Bambusa Vulgaris* stem extract, *Pisum Sativum* extract, *Apium Graveolens* Callus extract.

6. The formulation of claim 1, wherein the antioxidant component comprises at least one of *Vaccinium Vitis* Idea Fruit Extract, *Camellia* Sinesis Green Tea Leaf Extract, *Arnica, Astragalus* Membranaceus, Rutin, Hesperidin, and *Arnica Montana* Extract, *Pisum Sativum* extract, *Apium Graveolens* Callus extract and Naringin.

7. The formulation of claim 1 comprising from about 0.01 to about 30 wt. % of the prebiotic component; from about 0.00002 to about 5 wt. % of the bioavailable peptide component; from about 0.001 to about 10 wt. % of the matrix metalloproteinases inhibitor component; and 0.001 to 10 wt. % of the antioxidant component.

8. The formulation of claim 1 comprising from about 0.01 to about 25 wt. % of the prebiotic component; from about 0.002 to about 0.75 wt. % of the bioavailable peptide; from about 0.01 to about 5 wt. % of the matrix metalloproteinases inhibitor component; and from about 0.01 to about 5 wt. % of an antioxidant component.

9. The formulation of claim 1, wherein the carrier base is a lotion, a cream, or a hydrogel.

10. The formulation of claim 1, wherein the bioavailable peptide component comprises more than two bioavailable peptides.

11. The formulation of claim 1, wherein the matrix metalloproteinases inhibitor component comprises two or more metalloproteinases inhibitors.

12. The formulation of claim 1, wherein the prebiotic component comprises two or more prebiotics.

13. The formulation of claim 1, further comprising proteins.

14. The formulation of claim 1, further comprising retinoids.

15. The formulation of claim 1, wherein the carrier base comprises from about 40 to about 95 wt. % of the formulation.

16. The formulation of claim 1, wherein the matrix metalloproteinases inhibitor component is selected to function in coordination with the prebiotic component.

17. The formulation of claim 1, wherein the matrix metalloproteinases inhibitor component is selected to inhibit a plurality of matrix metalloproteinases.

18. The formulation of claim 17, wherein the matrix metalloproteinases inhibitor component inhibits any one or more of MMP-1, MMP-3, MMP-9 and MMP-12.

19. The formulation of claim 1, wherein the antioxidant component is selected to function in coordination with the prebiotic component.

20. The formulation of claim 1, wherein the antioxidant component is selected to scavenge or quench free radicals.

21. The formulation of claim 1, wherein the antioxidant component is selected to scavenge and quench superoxide anion, hydroxyl radical, and peroxide radical.

22. The formulation of claim 1, where in the pH of the formulation is from about 4.0 to about 6.0.

23. The formulation of claim 1, wherein the matrix metalloproteinases inhibitor component includes a matrix metalloproteinases inhibitor that also has antioxidant properties.

24. The formulation of claim 1, further comprising skin growth factors.

* * * * *